United States Patent
Segawa (10) Patent No.: US 7,770,725 B2
(45) Date of Patent: Aug. 10, 2010

(54) CAPSULE ENDOSCOPE STORAGE CASE

(75) Inventor: Hidetake Segawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 733 days.

(21) Appl. No.: 11/631,349

(22) PCT Filed: Nov. 28, 2005

(86) PCT No.: PCT/JP2005/021809

§ 371 (c)(1),
(2), (4) Date: Dec. 29, 2006

(87) PCT Pub. No.: WO2006/073030

PCT Pub. Date: Jul. 13, 2006

(65) Prior Publication Data

US 2008/0027267 A1    Jan. 31, 2008

(30) Foreign Application Priority Data

Jan. 5, 2005    (JP) ................................ 2005-000932

(51) Int. Cl.
*A61B 19/02* (2006.01)
*A61B 1/00* (2006.01)

(52) U.S. Cl. ................ 206/363; 206/439; 600/118; 600/121

(58) Field of Classification Search ............ 206/363, 206/438–439; 600/109–117, 130, 118, 121
See application file for complete search history.

(56) References Cited

U.S. PATENT DOCUMENTS

| | | | | |
|---|---|---|---|---|
| 4,697,703 A | | 10/1987 | Will | |
| 5,082,112 A | * | 1/1992 | Dunklee | 206/363 |
| 5,221,007 A | * | 6/1993 | Foos | 206/363 |
| 6,918,872 B2 | * | 7/2005 | Yokoi et al. | 600/130 |
| 7,117,993 B2 | | 10/2006 | Koike | |
| 7,295,226 B1 | * | 11/2007 | Meron et al. | 600/109 |
| 7,354,398 B2 | * | 4/2008 | Kanazawa | 600/109 |
| 7,553,274 B2 | * | 6/2009 | Miyake et al. | 600/121 |
| 2003/0168370 A1 | | 9/2003 | Merboth et al. | |
| 2004/0249291 A1 | | 12/2004 | Honda et al. | |
| 2004/0254455 A1 | | 12/2004 | Iddan | |
| 2005/0272973 A1 | | 12/2005 | Kawano et al. | |

FOREIGN PATENT DOCUMENTS

CN    86 2 08639 U    12/1987

(Continued)

OTHER PUBLICATIONS

Japanese Office Action dated Jun. 1, 2010 with English Translation.

*Primary Examiner*—Bryon P Gehman
(74) *Attorney, Agent, or Firm*—Scully, Scott, Murphy & Presser, P.C.

(57) ABSTRACT

In a storage case for accommodating a capsule endoscope in which a power supply can be operated by a predetermined magnetic force, when the capsule endoscope is retained by both a retaining portion provided in a blister pack and a hole portion provided in an inner cover portion while accommodated in the storage case, the blister pack, the inner cover portion, a sterilizing sheet, and a shield of the storage case are configured to cover an operable range for power supply of the capsule endoscope, and the storage case prevents malfunction of the capsule endoscope accommodated therein even if a magnet is unintentionally approximated.

6 Claims, 10 Drawing Sheets

FOREIGN PATENT DOCUMENTS

| | | |
|---|---|---|
| CN | 1448321 A | 10/2003 |
| CN | 2623644 | 7/2004 |
| EP | 1 598 000 A1 | 11/2005 |
| JP | 2003-210395 | 7/2003 |
| JP | 2003-523795 | 8/2003 |
| JP | 2004-167008 | 6/2004 |
| JP | 2004-261240 | 9/2004 |
| WO | WO 01/35813 A1 | 5/2001 |

* cited by examiner

CAPSULE ENDOSCOPE STORAGE CASE

TECHNICAL FIELD

The present invention relates to a capsule endoscope storage case which accommodates an intra-subject information acquiring device which is introduced into a subject to obtain image information of an inside of the subject, e.g., a swallowable capsule endoscope.

BACKGROUND ART

Recently, a capsule endoscope having an imaging function and a wireless communication function has made an appearance in the field of the endoscope. After the capsule endoscope is swallowed by a subject person as a subject (human body) for the purpose of an observation (examination), the capsule endoscope moves through the inside (body cavity) of organs such as the stomach and the small intestine according to peristaltic movement of the organ, and the capsule endoscope sequentially takes images using the imaging function until naturally discharged from a living body of the subject.

Image data taken in the body cavity by the capsule endoscope while the capsule endoscope moves in the organs, is sequentially transmitted to an external device provided at the outside of the body by the wireless communication function and stored in a memory provided in the external device. When the subject takes along the external device including the wireless communication function and the memory function, the subject can freely act even after swallowing the capsule endoscope until the capsule endoscope is discharged. After the observation, a doctor or a nurse can make a diagnosis based on the image in the body cavity displayed on display means such as a display from the image data stored in the memory of the external device.

An example of this kind of capsule endoscope includes a swallowable capsule endoscope disclosed in Patent Document 1. In a configuration of the capsule endoscope proposed in Patent Document 1, the capsule endoscope includes a reed switch which is turned on and off by an external magnetic field in order to control drive of the capsule endoscope, and the capsule endoscope is accommodated in a package including a permanent magnet which supplies the external magnetic field. That is, the reed switch included in the capsule endoscope is maintained in an off state under an environment in which the magnetic field having at least predetermined strength is applied, and the reed switch is turned on by decreasing the strength of the external magnetic field. Therefore, the capsule endoscope is not driven in the state in which the capsule endoscope is accommodated in the package. In swallowing the capsule endoscope, the capsule endoscope is taken out from the package and separated from the permanent magnet, so that the magnetic force has no influence on the capsule endoscope to start the drive of the capsule endoscope. In the capsule endoscope having the above configuration, the capsule endoscope can be prevented from being driven when the capsule endoscope is accommodated in the package, the image taking by the imaging function and the image signal transmission by the wireless function are performed after the capsule endoscope is taken out from the package.

Patent Document 1: International Publication No. 01/35813 Pamphlet

DISCLOSURE OF THE INVENTION

Problem to be Solved by the Invention

However, in the conventional apparatus, the magnetic field having the influence on the capsule endoscope acts on the outside of the package. Therefore, for example, when another magnet which generates a magnetic field negating the external magnetic field exists within the range of the external magnetic field, the capsule endoscope is not affected by the magnetic force, which results in a risk of generating of the malfunction of the capsule endoscope in the package.

As stated above, it is an object of the present invention to provide a capsule endoscope storage case which can prevent malfunction of the capsule endoscope accommodated in the storage case even if the magnet is unintentionally approximated.

Means for Solving the Problem

A capsule endoscope storage case, according to one aspect of the present invention, which accommodates a capsule endoscope whose power supply can be operated by a predetermined magnetic force, includes a surrounding unit that covers all directions of an operable range for the power supply of the accommodated capsule endoscope.

In the capsule endoscope storage case according to the present invention, the surrounding unit may include a retainer that retains the capsule endoscope in the capsule endoscope storage case; a sterilizing sheet that blocks a retention space area, having a sterilizing gas permeability; and a shield that shields a lower surface of the retainer.

In the capsule endoscope storage case according to the present invention, the retainer may include a first retainer and a second retainer which form the retention space area for retaining the capsule endoscope therebetween, the first retainer and the second retainer accommodating and retaining the capsule endoscope in the retention space area.

In the capsule endoscope storage case according to the present invention, one of the first retainer and the second retainer may be accommodated in the other one of the first retainer and the second retainer.

EFFECT OF THE INVENTION

According to the present invention, in the capsule endoscope storage case, the surrounding unit covers the whole of the operable range for power supply of the capsule endoscope accommodated in the storage case. Therefore, even if a magnet is unintentionally approximated, the surrounding unit prevents the magnet from entering the operable range for power supply, and the malfunction of the capsule endoscope accommodated in the storage case can be prevented.

EXPLANATIONS OF LETTERS OR NUMERALS

1 SUBJECT
2 CAPSULE ENDOSCOPE
2*a* REED SWITCH
2*b* OPERABLE RANGE FOR POWER SUPPLY
3 RECEIVING DEVICE
4 DISPLAY DEVICE
5 PORTABLE RECORDING MEDIUM
11 AIRTIGHT CONTAINER
11*a* FRONT-HEAD COVER
11*a*1 MIRROR-finished PORTION
11*b* BODY PORTION COVER
20 LIGHT EMITTING ELEMENT (LED)
21 LED DRIVING CIRCUIT
22 SOLID-STATE IMAGING ELEMENT
23 CCD DRIVING CIRCUIT
24 RF TRANSMITTING UNIT
25 TRANSMITTING ANTENNA UNIT
26 SYSTEM CONTROL CIRCUIT
27 IMAGING LENS
29 BATTERY
31 RECEIVING JACKET
32 EXTERNAL DEVICE
40 STORAGE CASE
40*a* RETENTION SPACE AREA
40*b* PASSAGE
41 BLISTER PACK
41*a*, 42*a* CYLINDRICAL PORTION
41*b*, 42*b* HANDGRIP PORTION
41*c*, 42*c* EDGE PORTION
41*d*, 42*d* PROJECTION PORTION
41*e*, 42*e* BOTTOM FACE
41*e*1 OUTSIDE BOTTOM FACE
41*e*2 INSIDE BOTTOM FACE
41*e*3 RETAINING PORTION
41*e*4 PROJECTION PORTION
42 INNER COVER PORTION
42*e*1 HOLE PORTION
42*e*2 PROJECTION
42*e*3 STEP PORTION
43 STERILIZING SHEET
44 SHIELD

BEST MODES FOR CARRYING OUT THE INVENTION

Exemplary embodiments of a capsule endoscope storage case according to the invention will be described in detail with reference to FIGS. 1 to 13. The invention is not limited to the embodiments, but various modifications and changes could be made without departing from the scope of the invention.

First Embodiment

Figure 1:
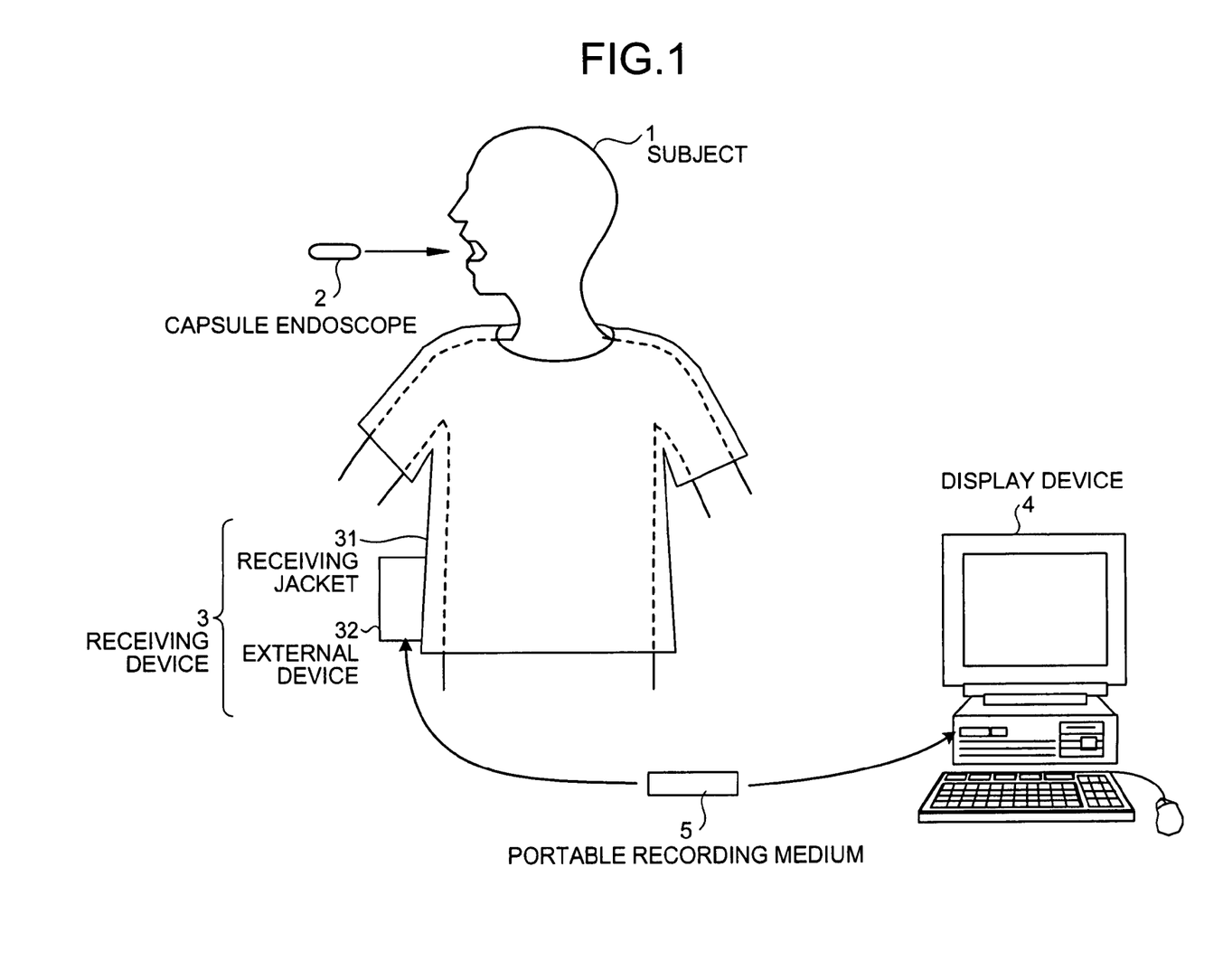
FIG. 1 is a system conceptual view showing a concept of a wireless type intra-subject information obtaining system according to the invention.

FIG. 1 is a system conceptual view showing a concept of a wireless type intra-subject information obtaining system according to the invention. Referring to FIG. 1, the capsule endoscope system includes a swallowable capsule endoscope 2, a receiving device 3, a display device 4, and a portable recording medium 5. The swallowable capsule endoscope 2 which is of the wireless type intra-subject information acquiring device is introduced into the body cavity of a subject 1. The receiving device 3 which is of the external device is arranged outside the subject 1, and the receiving device 3 performs the wireless communication about various kinds of information with the capsule endoscope 2. The display device 4 displays the image based on the data received by the receiving device 3. The portable recording medium 5 performs data input and output between the receiving device 3 and display device 4.

Figure 2:
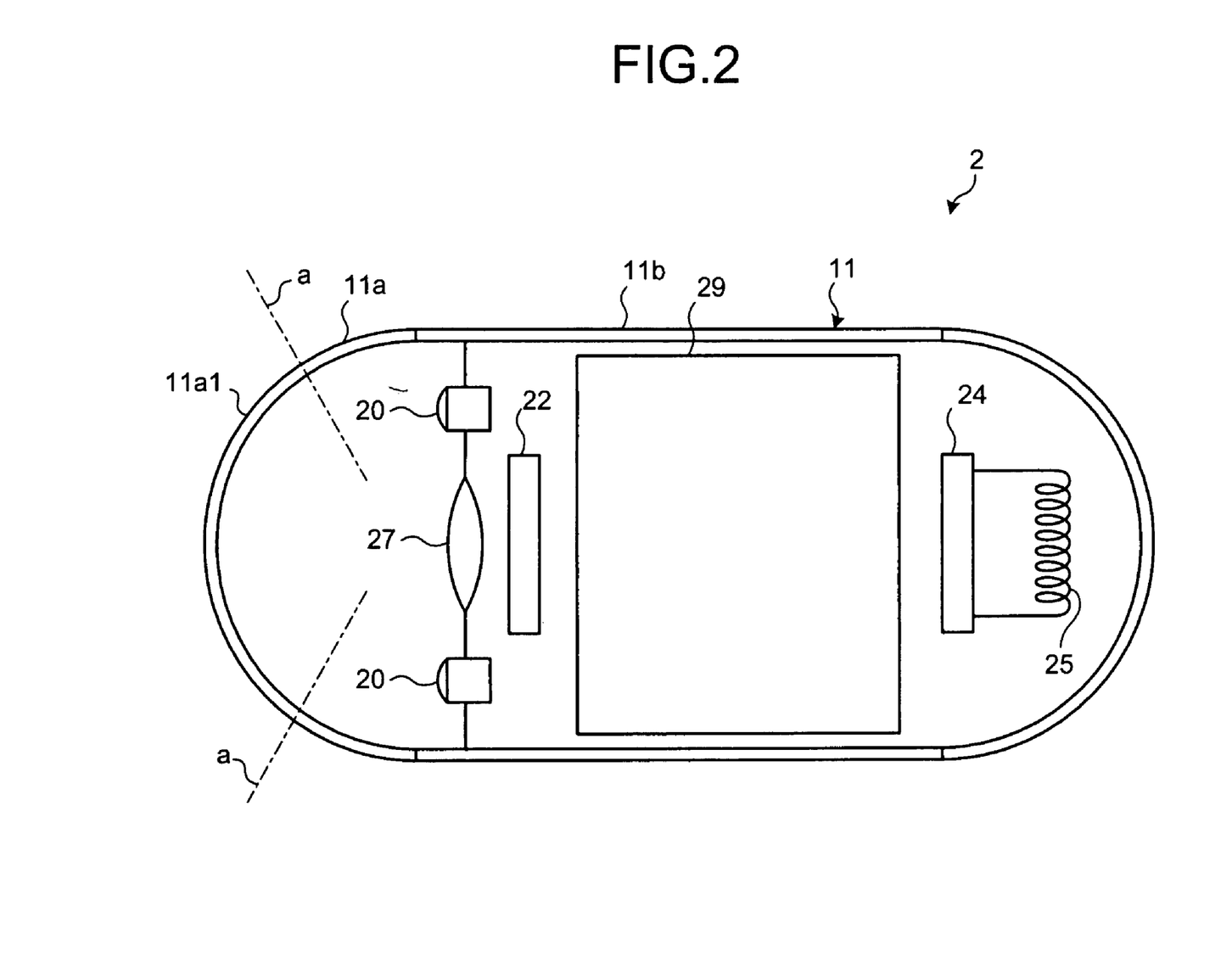
FIG. 2 is a sectional side view showing a schematic configuration of a capsule endoscope shown in FIG. 1.

As shown in a sectional side view of FIG. 2, the capsule endoscope 2 includes components such as an airtight container 11, plural light emitting elements 20, a solid-state imaging element 22, an imaging lens 27, an RF transmitting unit 24, a transmitting antenna unit 25, and a battery 29. The airtight container 11 is an exterior case. The light emitting elements 20 such as LEDs are located in the airtight container 11 to emit light for illuminating a subject region in the body cavity. The solid-state imaging element 22 (hereinafter representatively referred to as "CCD 22") such as CCD and CMOS receives the light reflected from the subject region to image the subject region. The imaging lens 27 images a subject image on CCD 22. The RF transmitting unit 24 modulates the image information obtained by CCD 22 into an RF signal to transmit the RF signal. The transmitting antenna unit 25 emits a radio wave of the RF signal.

The airtight container 11 has a size enough to be swallowed by a human. In the airtight container 11, an exterior case which seals the inside in a liquid-tight manner by fitting elastically a substantially hemispherical front-head cover 11*a* in a cylindrical body-portion cover 11*b* is formed. The front-head cover 11*a* is formed in the substantially hemispherical dome shape, and the backside of the dome is opened in the circular shape. The front-head cover 11*a* is formed by a transparent member having a transparent or translucent property, such as cycloolefine polymer or polycarbonate which is preferably ensure optical performance and strength. The front-head cover 11*a* has a later-mentioned mirror-finished portion 11*a*1 in which mirror polishing is performed to a surface thereof, so that the illumination light from the light emitting element 20 can be transmitted to the outside through the airtight container 11 while the light reflected from the subject is transmitted to the inside. The mirror-finished portion 11*a*1 is formed in a predetermined mirror polished range (range shown by an alternate long and short dash line a and a in FIG. 2) determined by an imaging range of the solid-state imaging element 22 and the like.

The body-portion cover 11*b* is a member which is located at a rear end of the front-head cover 11*a* to cover the above components. The body-portion cover 11*b* integrally forms a cylindrical body portion and a rear end portion having a substantially hemispherical dome shape, and the front side of the body portion is opened in the circular shape. The body-portion cover 11b is made of polysulfone which preferably secure the strength. In the body-portion cover 11b, the later-mentioned illumination means, the imaging means, and the battery 29 are accommodated in the body portion, and wireless transmitting means is accommodated in the rear end portion.

Figure 3:
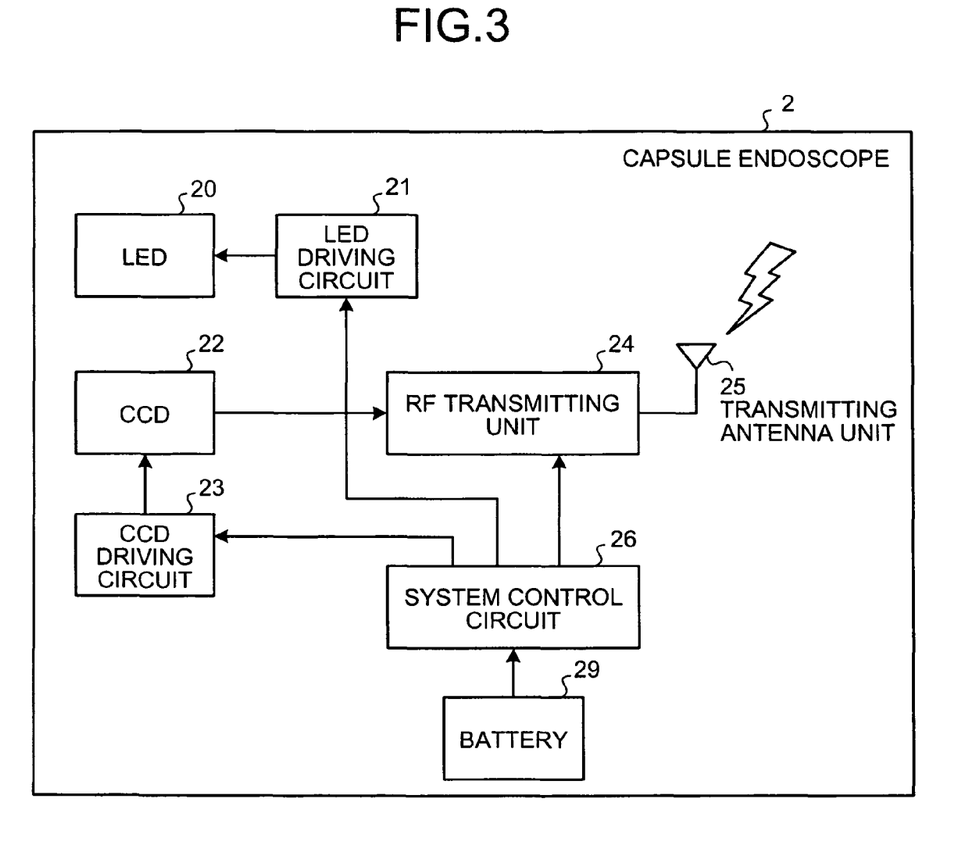
FIG. 3 is a block diagram showing an internal configuration of the capsule endoscope shown in FIG. 2.

As shown in a block diagram of FIG. 3, the capsule endoscope 2 includes LED 20 and an LED driving circuit 21, CCD 22, a CCD driving circuit 23, an RF transmitting unit 24, and a transmitting antenna unit 25 in the inside of the airtight container 11. LED 20 is of the illumination means, and the LED driving circuit 21 controls the drive state of LED 20. CCD 22 as the imaging means images the image (intra-subject information) in the body cavity which is of the light reflected from the region illuminated by LED 20 through an imaging lens 27. The CCD driving circuit 23 controls the drive state of CCD 22. The RF transmitting unit 24 is of the wireless transmitting means.

The capsule endoscope 2 also includes a system control circuit 26 which controls the operations of the LED driving circuit 21, the CCD driving circuit 23, and the RF transmitting unit 24. Therefore, the capsule endoscope 2 is operated so as to obtain the image data of the examined region illuminated by LED 20 through CCD 22 while the capsule endoscope 2 is introduced in the subject 1. The obtained image data is converted into the RF signal by the RF transmitting unit 24, and the RF signal is transmitted to the outside of the subject 1 through the transmitting antenna unit 25. The capsule endoscope 2 also includes the battery 29 which supplies electric power to the system control circuit 26, and the system control circuit 26 has a function of distributing drive electric power supplied from the battery 29 to other component (function performing means).

For example, the system control circuit 26 includes a switch element and a latch circuit. The switch element has a function of switching connections between the battery 29 and the components. The latch circuit turns on the switch element when the magnetic field is applied from the outside, and the latch circuit maintains the on state after that to supply the drive electric power from the battery 29 to each component in the capsule endoscope 2. In the embodiment, the imaging means having the imaging function included in the capsule endoscope 2, the illumination means having the illumination function, and the wireless transmitting means having the wireless function are collectively called the function performing means for performing the predetermined function. Specifically, the components except for the system control circuit 26 are the function performing means for performing the predetermined function set in advance.

As shown in FIG. 1, the receiving device 3 functions as wireless receiving means for receiving the body-cavity image data wirelessly transmitted from the capsule endoscope 2. The receiving device 3 is attached to the subject 1, and the receiving device 3 includes a receiving jacket 31 and an external device 32. The receiving jacket 31 has plural receiving antennas (not shown) and the external device 32 performs the signal processing to the received wireless signal.

The display device 4 displays the body-cavity image taken by the capsule endoscope 2. The display device 4 is realized by a workstation or the like which displays the image based on the data obtained by the portable recording medium 5. Specifically, the display device 4 may be formed to directly display the image with a CRT display, a liquid crystal display, and the like, or the display device 4 may be formed by a printer and the like which output the image in another kinds of the medium.

The portable recording medium 5 can be connected to the external device 32 and the display device 4, and the portable recording medium 5 is attached to the external device 32 and the display device 4 to have a structure in which the information can be output or recorded in connecting the portable recording medium 5. In the embodiment, the portable recording medium 5 is inserted into the external device 32 to record the data transmitted from the capsule endoscope 2 while the capsule endoscope 2 moves in the body cavity of the subject 1. After the capsule endoscope 2 is discharged from the subject 1, namely, after the imaging in the subject 1 is finished, the portable recording medium 5 is taken out from the external device 32 and inserted into the display device 4, and the data recorded in the portable recording medium 5 is read by the display device 4. For example, the portable recording medium 5 is formed by CompactFlash (registered trademark) memory or the like, and the data can indirectly be input and output between the external device 32 and the display device 4 through the portable recording medium 5. Unlike the case where the external device 32 and the display device 4 are directly connected by a cable, the subject 1 can freely be moved in imaging the body cavity.

Figure 4:
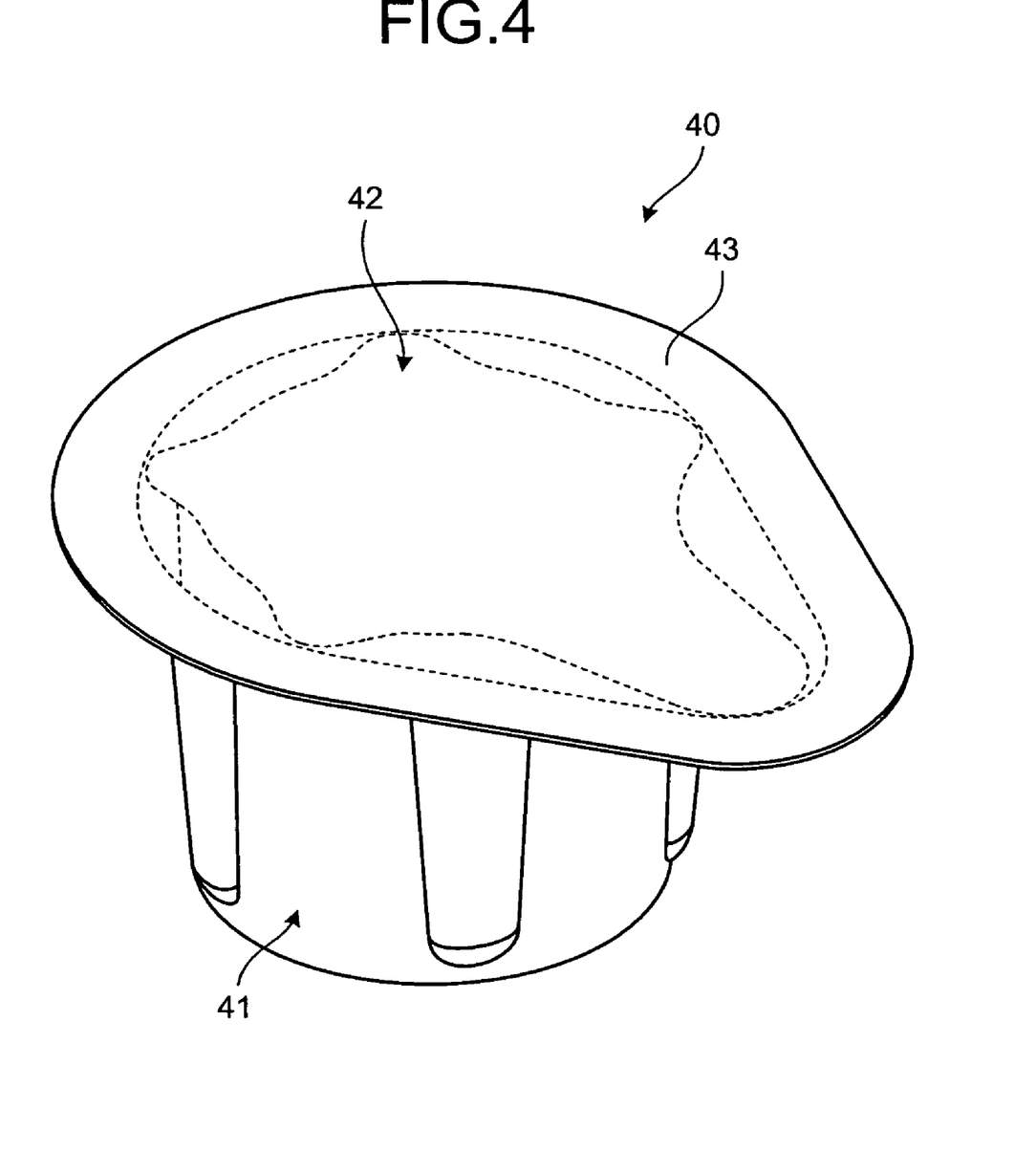
FIG. 4 is a perspective view showing a configuration of a storage case which accommodates the capsule endoscope.
Figure 8:
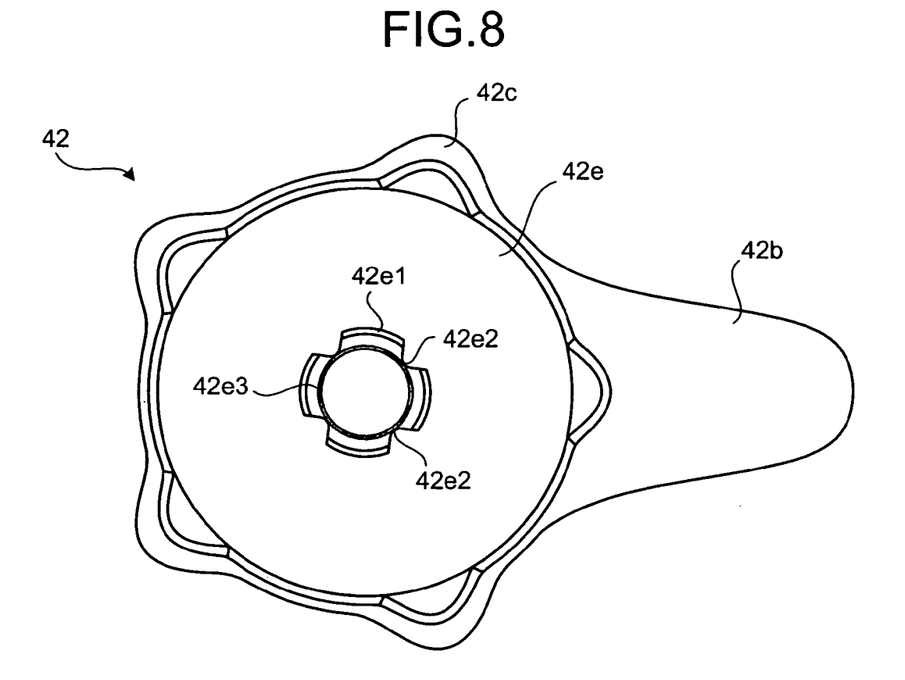
FIG. 8 is a top view showing a top face of an inner cover portion according to a first embodiment shown in FIG. 5.
Figure 9:
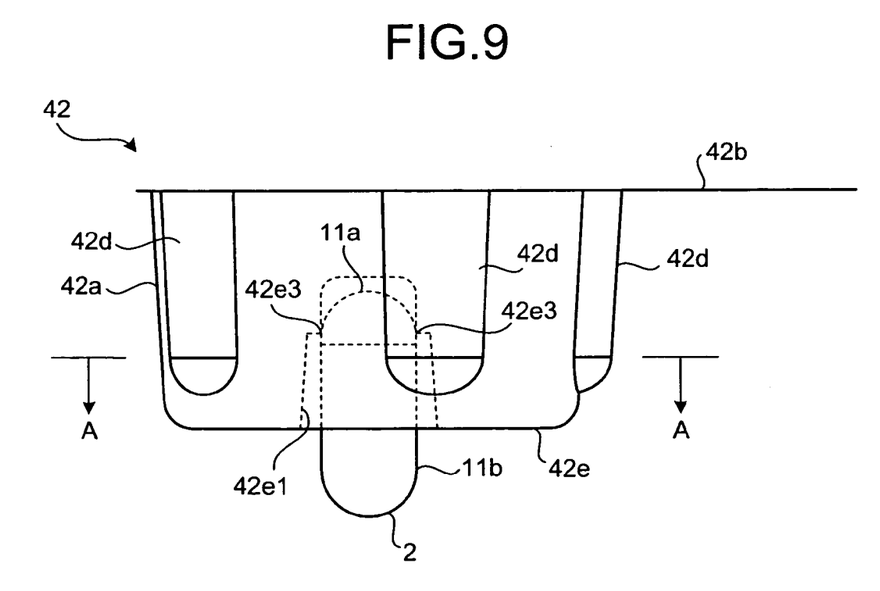
FIG. 9 is a side view showing a side face of the inner cover portion according to the first embodiment.
Figure 10:
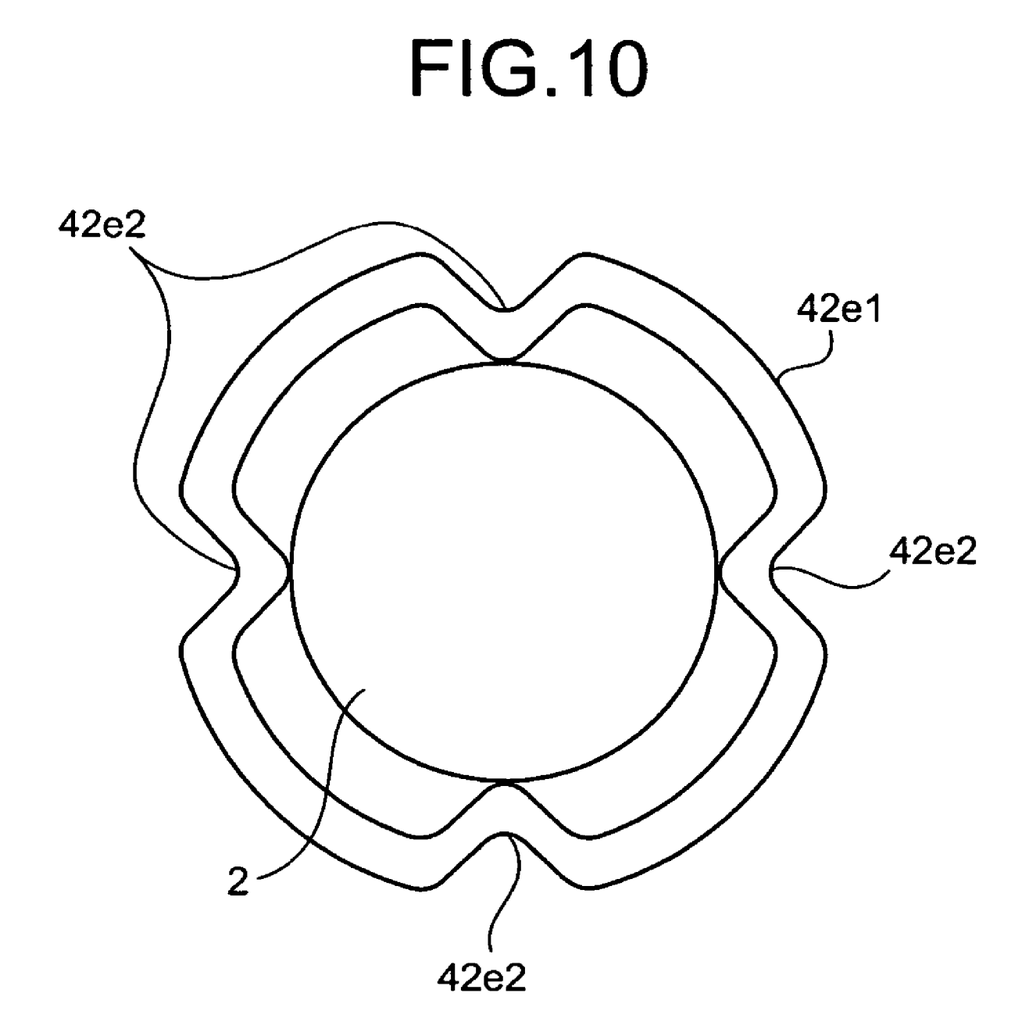
FIG. 10 is a sectional view showing an enlarged section A-A of a hole portion shown in FIG. 9.
Figure 11:
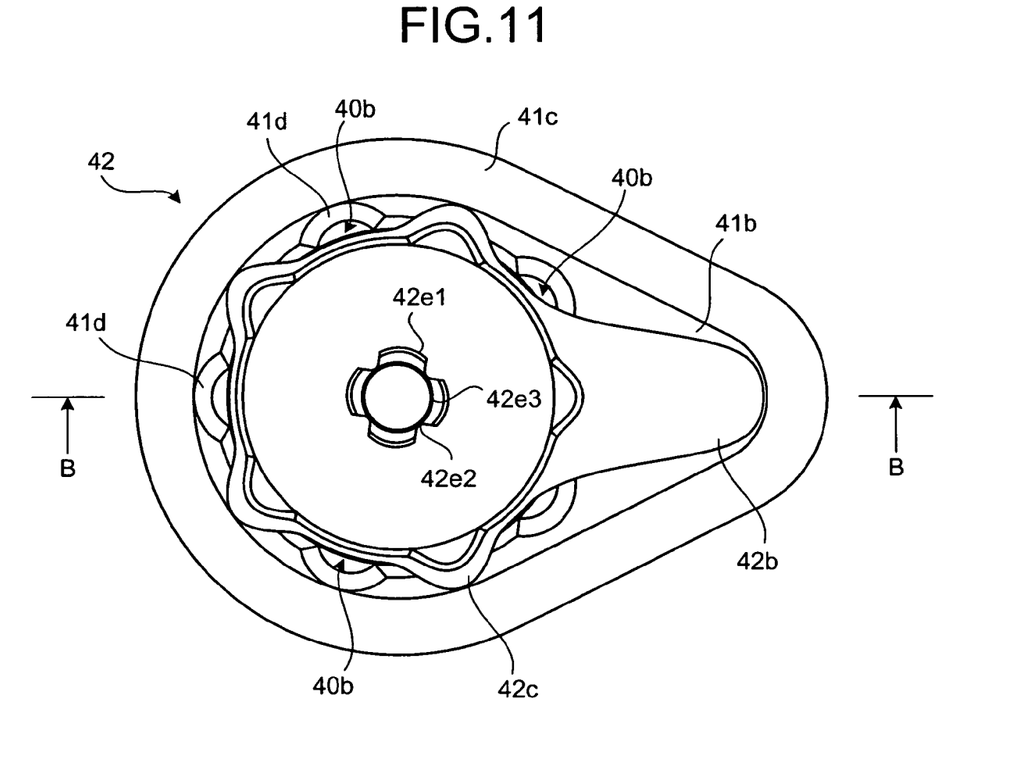
FIG. 11 is a top view showing the top face of the storage case shown in FIG. 5.
Figure 12:
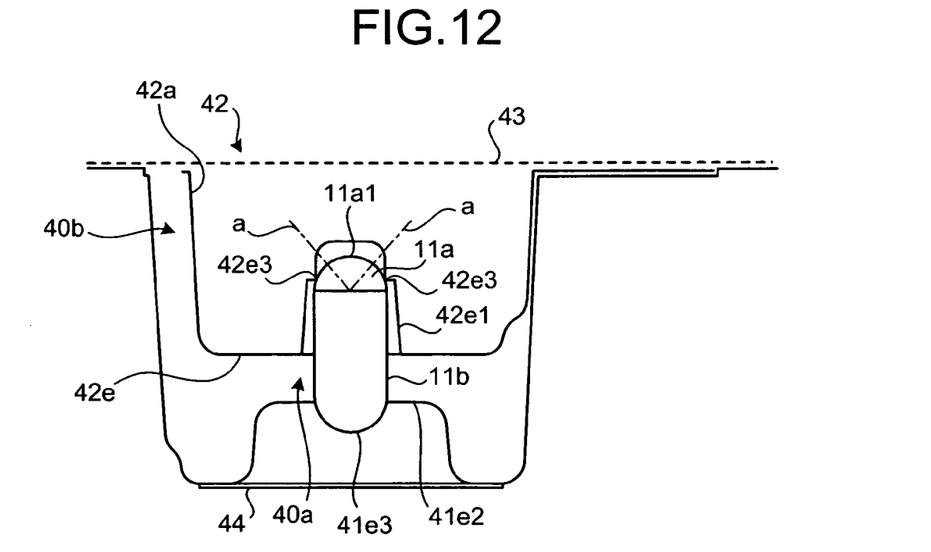
FIG. 12 is a sectional view taken on line B-B of FIG. 11.

It is necessary that the capsule endoscope having the function performing means be sterilized and maintained in the sterilized state before the use of the capsule endoscope for the subject. Therefore, in the embodiment, the capsule endoscope 2 is accommodated in a storage case in which the sterilization can be performed. The storage case according to the first embodiment will be described below with reference to FIGS. 4 to 12. FIG. 4 is a perspective view showing a configuration of the storage case which accommodates the capsule endoscope, FIG. 5 is a perspective view showing an example of the case where a sterilizing sheet is removed from the storage case shown in FIG. 4, FIG. 6 is a top view showing a top face of the storage case shown in FIG. 5, FIG. 7 is a side view showing a side face of the storage case, FIG. 8 is a top view showing a top face of an inner cover portion according to the first embodiment shown in FIG. 5, FIG. 9 is a side view showing the side face of the inner cover portion according to the first embodiment, FIG. 10 is a sectional view showing an enlarged section A-A of a hole portion shown in FIG. 9, FIG. 11 is a top view showing the top face of the storage case shown in FIG. 5, and FIG. 12 is a sectional view taken on line B-B of FIG. 11.

Figure 5:
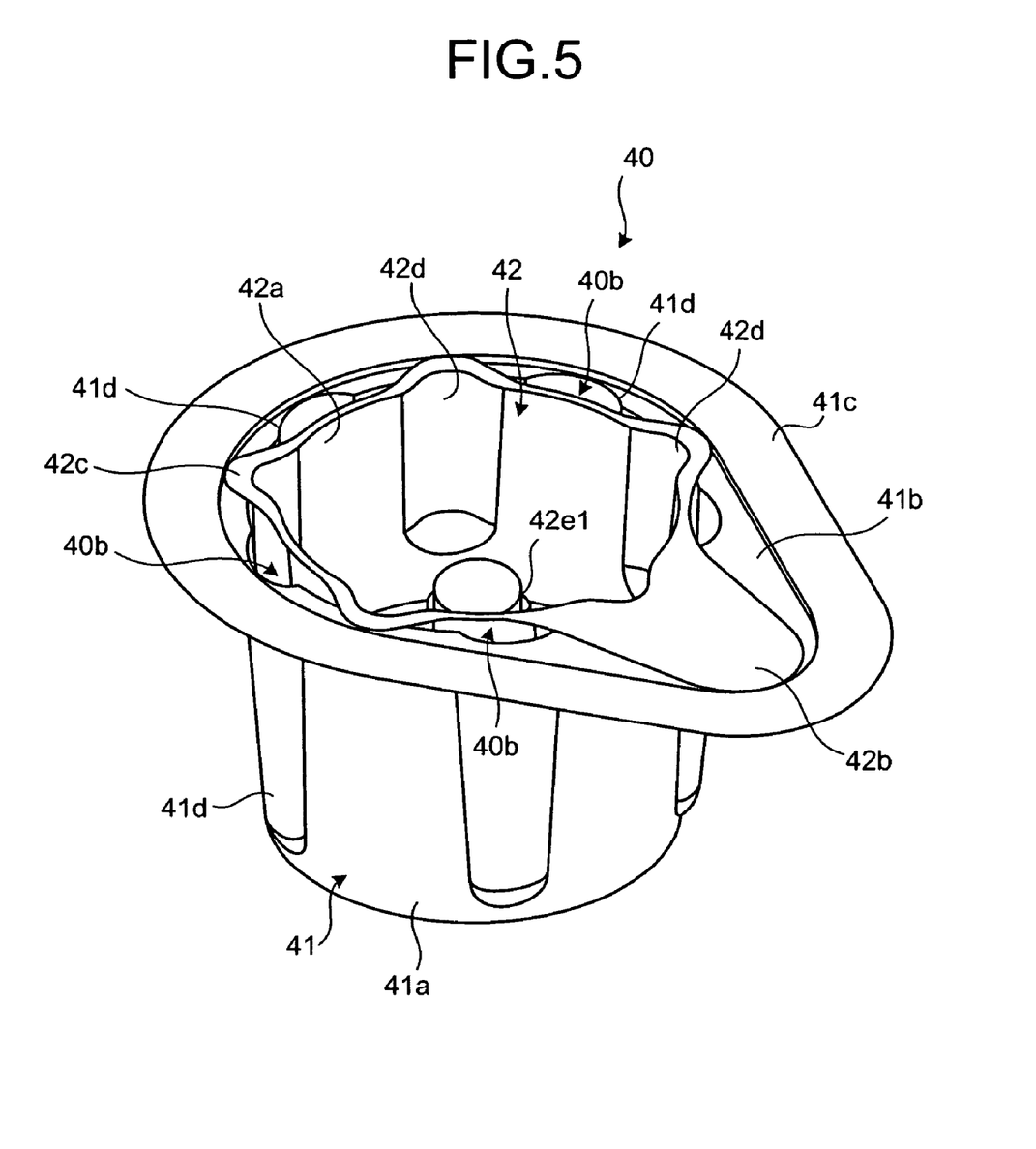
FIG. 5 is a perspective view showing an example of the case where a sterilizing sheet is removed from the storage case shown in FIG. 4.

In FIGS. 4 and 5, a storage case 40 includes a blister pack 41, an inner cover portion 42, a sterilizing sheet 43, and a shield 44 (see later-mentioned FIG. 7). The blister pack 41 is formed by an outside storage portion which can accommodate the capsule endoscope 2 therein. The inner cover portion 42 is included in the blister pack 41, and the inner cover portion 42 is formed by an inside storage portion in which the capsule endoscope 2 is retained with the blister pack 41. The sterilizing sheet 43 is provided on a top face of the blister pack 41 to close an opening of the blister pack 41. The shield 44 shields a lower surface of the blister pack 41. The blister pack 41 and the inner cover portion 42 constitute the first retainer and the second retainer according to the invention respectively, and the shield 44 constitutes the shield according to the invention.

Figure 6:
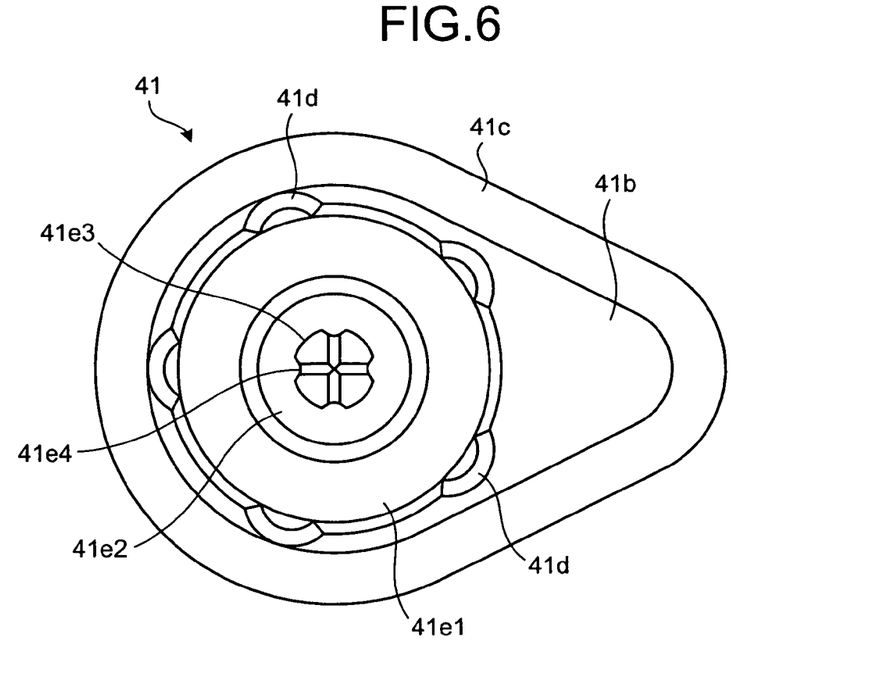
FIG. 6 is a top view showing a top face of the storage case shown in FIG. 5.
Figure 7:
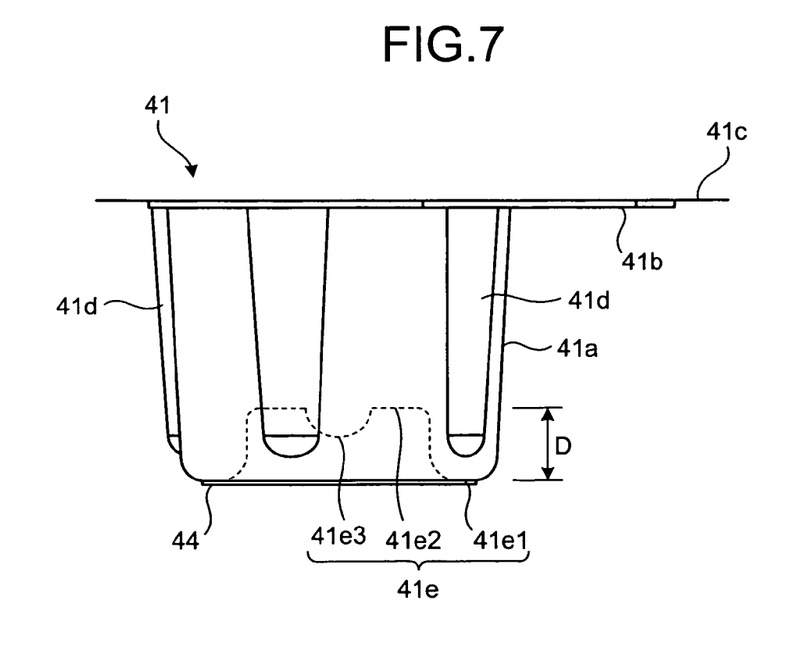
FIG. 7 is a side view showing a side face of the storage case.

As shown in FIGS. 6 and 7, the blister pack 41 includes a cylindrical portion 41a, a handgrip portion 41b, an edge portion 41c, and plural projection portions 41d. The cylindrical portion 41a has a bottom. The handgrip portion 41b having a tongue shape is provided in a part of an upper edge of the opening of the cylindrical portion 41a. The edge portion 41c is provided in the upper edge of the opening of the cylindrical portion 41a and in an outer periphery of the handgrip portion 41b. The projection portions 41d are provided in a peripheral surface of the cylindrical portion 41a, and the projection portions 41d having a substantially semi-cylindrical shape are projected outward from the inside of the cylindrical portion 41a.

The cylindrical portion 41a has a bottom face 41e including an outside bottom face 41e1 and an inside bottom face 41e2. The outside bottom face 41e1 is provided on the outer periphery of the cylindrical portion 41a, and the inside bottom face 41e2 is provided in the substantially central portion of the outside bottom face 41e1. The inside bottom face 41e2 is formed in a disc shape having a predetermined radius. The outside bottom face 41e1 is formed by a bottom face which is projected from the position of the inside bottom face 41e2 toward the outside (opposite direction to the opening direction) of the cylindrical portion 41a, and the lower surface of the outside bottom face 41e1 is formed in a hollow toroidal shape having a predetermined width. As shown in FIG. 7, a difference of elevation D is generated between the outside bottom face 41e1 and the inside bottom face 41e2. A substantially hemispherical retaining portion 41e3 is provided in the central portion of the inside bottom face 41e2. The retaining portion 41e3 is recessed from the position of the inside bottom face 41e2 toward the direction of the outside bottom face 41e1. The retaining portion 41e3 retains the dome-shape rear end portion constituting the body-portion cover 11b of the capsule endoscope 2. In the inside of the retaining portion 41e3, the cross-shape projection portion 41e4 is provided toward the opening direction, which enables a sterilizing gas to invade into the rear end portion of the body-portion cover 11b retained by line contact to evenly sterilize the whole of the rear end portion. The projection portion 41e4 may be formed by plural projections to retain the rear end portion with each of the projections by point contact.

The handgrip portion 41b is formed by a plate-shape member whose top face has a substantially triangular shape, and the handgrip portion 41b is formed such that a later-mentioned handgrip portion 42b of the inner cover portion 42 can abut on the top face of the handgrip portion 41b as shown in FIG. 5. The edge portion 41c has a predetermined width. The edge portion 41c is provided in the upper edge of the opening of the cylindrical portion 41a and in the outer periphery of the handgrip portion 41b while formed in the step shape higher than that of the handgrip portion 41b by one step, which suppresses the movement of the handgrip portion 42b of the inner cover portion 42 which abuts on the handgrip portion 41b. A height of the edge portion 41c is configured so as to be equal to or higher than thicknesses of the handgrip portion 42b and an edge portion 42c of the inner cover portion 42 which abut on the handgrip portion 41b, so that the sterilizing sheet 43 can adhere to the top face of the edge portion 41c while the inner cover portion 42 is accommodated in the blister pack 41.

The projection portion 41d is formed by the substantially semi-cylindrical projection provided in a lengthwise direction of the cylindrical portion 41a. The projection portion 41d has the largest radius at the upper end (opening side of the cylindrical portion 41a), and the radius is gradually decreased toward the lower end (side of the bottom face 41e). The plural projection portions 41d having the same shape are arranged at substantially equal intervals along the lengthwise direction of the cylindrical portion 41a. In the projection portions 41d, the upper end is opened, and the bottom face having the semi-dome shape is formed at the lower end. In the embodiment, the five projection portions 41d are arranged at substantially equal intervals in the peripheral surface of the cylindrical portion 41a (see FIG. 6).

As shown in FIGS. 8 and 9, the inner cover portion 42 includes a cylindrical portion 42a, the handgrip portion 42b, the edge portion 42c, and plural projection portions 42d. The cylindrical portion 42a has a bottom. The handgrip portion 42b having a tongue shape is provided in a part of the upper edge of the opening of the cylindrical portion 42a. The edge portion 42c is provided in the upper edge of the opening of the cylindrical portion 42a so as to be continued into the handgrip portion 42b. The projection portions 42d having the substantially semi-cylindrical shape are projected outward from the inside of the cylindrical portion 42a.

As shown in FIGS. 8 to 12, the cylindrical portion 42a has a bottom face 42e, and a hole portion 42e1 is provided in the central portion of the bottom face 42e to retain the capsule endoscope 2. The hole portion 42e1 is formed in a substantially cylindrical shape having a projection in cross section, and the hole portion 42e1 has the top face which is projected from the position of the bottom face 42e toward the inside (opening direction) of the cylindrical portion 42a (see FIG. 12). An inner diameter of the hole portion 42e1 is slightly larger than an outer diameter of the capsule endoscope 2. In an inner periphery of the hole portion 42e1, plural linear projections 42e2 (four projections 42e2 in the embodiment) are formed in the lengthwise direction toward the opening of the hole portion 42e1. A step portion 42e3 is provided on the upper face side of the hole portion 42e1, and the inner diameter of the step portion 42e3 is smaller than the inner diameter on the opening side of the hole portion 42e1. As shown in FIG. 12, when the inner cover portion 42 is accommodated in the blister pack 41, the bottom face 42e including the hole portion 42e1 of the cylindrical portion 42a and the inside bottom face 41e2 including the retaining portion 41e3 of the blister pack 41 constitute the retention space area 40a according to the invention, which allows the capsule endoscope 2 to be accommodated and retained.

In the embodiment, as shown in FIGS. 9 and 12, when the side of the front-head cover 11a of the capsule endoscope 2 is inserted into the hole portion 42e1, the front-edge portion of the step portion 42e3 retains a part of the front-head cover 11a with the line contact while the projection 42e2 retains a part of the body-portion cover 11b of the airtight container 11 with the line contact such that the mirror-finished portion 11a1 located within the alternate long and short dash lines a and a does not come into contact with a component part of the hole portion 42e1 including the projection 42e2 and step portion 42e3. The projections 42e2 are not limited to one which is linearly formed in the lengthwise direction of the hole portion 42e1. Alternatively, the plural projection portions are provided in the hole portion 42e1, and a part of the body-portion cover 11b of the airtight container 11 may be retained with the point contact by the plural projection portions.

The handgrip portion 42b is formed by a substantially triangular plate-shape member whose top face is substantially smaller than the handgrip portion 41b, and the handgrip portion 42b is integral to the edge portions 42c provided in the upper edge of the opening of the cylindrical portion 42a as shown in FIGS. 8 and 11. The handgrip portion 42b is configured to abut on the handgrip portion 41b of the blister pack 41 when the inner cover portion 42 is accommodated in the blister pack 41. The edge portion 42c is provided in the upper edge of the opening of the cylindrical portion 42a, and the edge portion 42c is configured to abut on the upper edge of the opening of the blister pack 41 when the inner cover portion 42 is accommodated in the blister pack 41. As described above, the thicknesses of the handgrip portion 42b and edge portion 42c are not more than the thickness of the edge portion 41c of the blister pack 41. When the inner cover portions 42 are accommodated in the blister pack 41, the edge portion 41c restricts the movement of the handgrip portion 42b within the range of the width of the handgrip portion 41b. When the sterilizing sheet 43 adheres to the top face of the edge portion 41c, the whole of the inner cover portion 42 including the handgrip portion 42b and edge portions 42c is accommodated in the blister pack 41.

Each of the projection portions 42d is formed by the substantially semi-cylindrical shape provided in the lengthwise direction of the cylindrical portion 42a, and the projection portions 42d are arranged at substantially equal intervals along the lengthwise direction of the cylindrical portion 42a. In the projection portions 42d, the upper end is opened, and the bottom face having the semi-dome shape is formed in the lower end. In the embodiment, the five projection portions 42d are arranged at substantially equal intervals in the peripheral surface of the cylindrical portion 42a. In the state in which the inner cover portion 42 is accommodated in the blister pack 41 while the handgrip portions 41b and 42b abut on each other, tip portions of the projection portions 42d are formed to be able to come into contact with the inner peripheral surface of the cylindrical portion 41a at the positions where the projection portions 42d do not face the projection portions 41d of the blister pack 41. Therefore, looseness of the inner cover portion 42 is prevented in the blister pack 41.

As shown in FIGS. 5, 11 and 12, a passage 40b which is of a gap according to the invention is formed between the inner peripheral surface of the projection portion 41d of the blister pack 41 and the outer peripheral surface of the cylindrical portion 42a of the inner cover portion 42. Therefore, the sterilizing gas invading from the outside through the sterilizing sheet 43 can pass through the passage 40b. The passage 40b and the retention space area 40a are communicated with each other, which enables the sterilizing gas passing through the passage 40b to reach the retention space area 40a.

Figure 13:
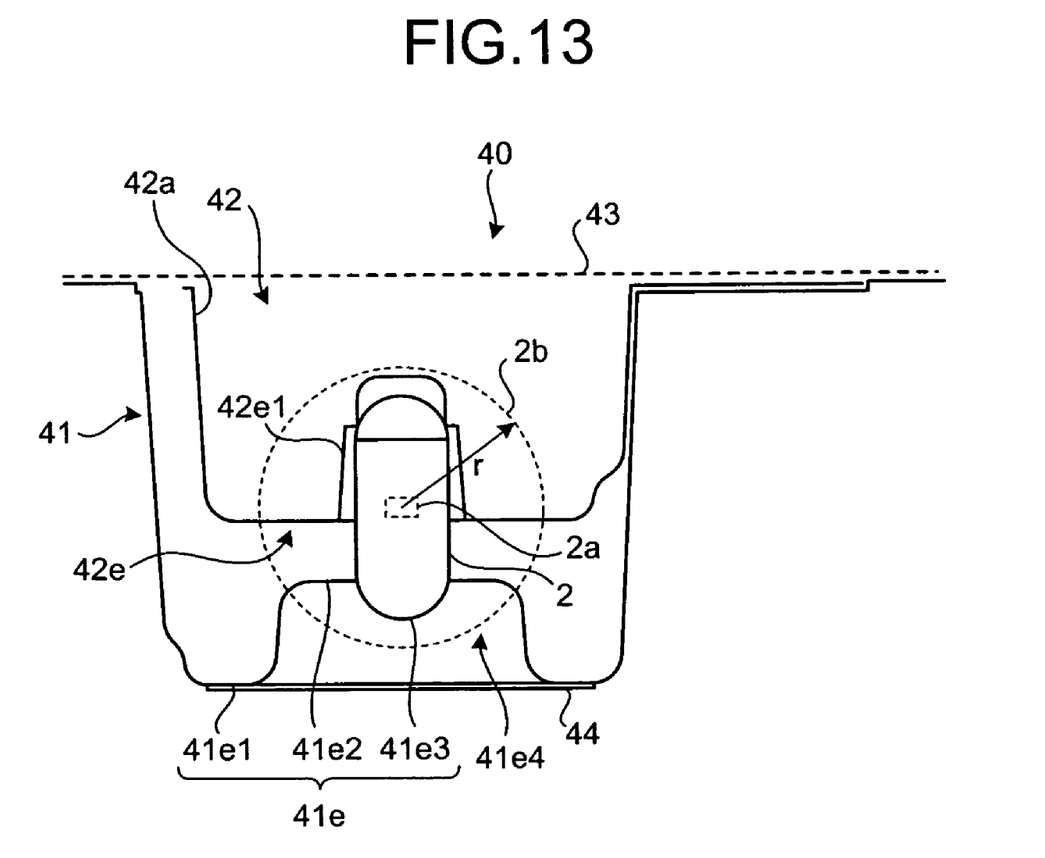
FIG. 13 is a sectional view similar to FIG. 12 for explaining an operable range for power supply.

As shown in FIG. 13, the capsule endoscope 2 has a reed switch 2a for the supply of electric power therein, and the reed switch 2a is turned on and off by the external magnetic field. When the reed switch 2a is turned on to supply the electric power from the battery 29 to each of the function performing means, LED 20 shown in FIG. 2 informs the outside of the supply of electric power by blinking. The reed switch 2a is provided in the substantially central portion in the lengthwise direction of the capsule endoscope 2. The reed switch 2a has a spherical operable range for power supply 2b. In the operable range for power supply 2b, the reed switch 2a is turned on to be able to operate the power supply, when the permanent magnet (not shown) is approximated to the range within a radius r of the reed switch 2a to apply the predetermined magnetic force. In the embodiment, for example, the diameters of the bottom face 41e of the blister pack 41 and the bottom face 42e of the inner cover portion 42 are larger than the diameter 2r of the operable range for power supply 2b. In the embodiment, when the capsule endoscope 2 is retained by the retaining portion 41e3 of the blister pack 41 and the hole portion 42e1 of the inner cover portion 42, the operable range for power supply 2b includes the inside bottom face 41e2 and the retaining portion 41e3, the operable range for power supply 2b is set within the range of the heights of the outside bottom face 41e1 and inside bottom face 41e2, the operable range for power supply 2b includes the hole portion 42e1, and the operable range for power supply 2b is set within the range of the height of the cylindrical portion 42a.

Therefore, during the use of the capsule endoscope 2, the sterilizing sheet 43 is peeled off from the storage case 40, the magnetic material (magnet) is accommodated inside the cylindrical portion 42a of the inner cover portion 42, and the reed switch is turned on by the magnetic field of the accommodated magnetic material. Therefore, the blinking state of LED 20 can be confirmed from the transparent or semi-transparent hole portion 42e1. That is, the hole portion 42e1 has the function of facilitating the confirmation of the LED blinking in addition to the function of retaining and protecting the capsule endoscope 2.

The shield 44 is formed in the disc shape, and the shield 44 is fixed to the outside bottom face 41e1 so as to shield the bottom face 41e which is of the lower surface of the blister pack 41. The diameter of the shield 44 is formed to be substantially equal to the diameter of the bottom face 41e, so that the shield 44 can shield a space region (region where the inside bottom face 41e2 and the retaining portion 41e3 are formed) 41e4 inside the outside bottom face 41e1 where the operable range for power supply 2b exists from the outside.

Thus, in the embodiment, the whole of the operable range for power supply 2b of the capsule endoscope 2 accommodated in the storage case 40 is covered with the blister pack 41, the inner cover portion 42, the sterilizing sheet 43, and the shield 44, so that the magnet does not enter the operable range for power supply 2b even if the magnet is unintentionally approximated to the storage case 40. Therefore, because the magnetic force of the magnet does not affect the reed switch, the malfunction can be prevented in the capsule endoscope accommodated in the storage case.

In the embodiment, the passage and the retention space area communicated with the passage are formed between the blister pack and the inner cover portion, and the capsule endoscope is accommodated and retained with the line contact in the formed retention space area. Therefore, the capsule endoscope can securely be retained. Furthermore, the opening of the blister pack is closed by the sterilizing sheet having the sterilizing gas permeability such that the passage and the retention space area are closed, so that the sterilizing gas invades into the contact portions of the capsule endoscope through the passage and retention space area to perform the gas sterilization. Therefore, the whole of the capsule endoscope accommodated in the storage case can be sterilized evenly and securely.

INDUSTRIAL APPLICABILITY

As stated above, the capsule endoscope storage case according to the present invention is useful to the medical observation apparatus such as the capsule endoscope which is introduced to the inside of the human body to observe the examined region. Particularly, the invention is proper to prevent the malfunction of the capsule endoscope accommodated in the storage case against the unintended approximation of the magnet.

The invention claimed is:

1. A capsule endoscope storage case for accommodating a capsule endoscope having a switch for as power supply of the capsule endoscope, the switch to be turned on by a predetermined magnetic force of a magnet disposed within an operable range of the switch of the capsule endoscope, the storage case comprising a housing designed for accommodating the capsule endoscope so that in all directions of the operable range of the switch of the capsule endoscope, the magnet disposed externally of the storage case does not affect the switch.

2. The capsule endoscope storage case according to claim 1, wherein the housing includes
a retainer for retaining the capsule endoscope in the capsule endoscope storage case;
a sterilizing sheet that blocks a retention space area, the sterilizing sheet having a sterilizing gas permeability; and
a shield that shields a lower surface of the retainer.

3. The capsule endoscope storage case according to claim 2, wherein the retainer includes a first retainer and a second retainer which form the retention space area for retaining the capsule endoscope therebetween, the first retainer and the second retainer for accommodating and retaining the capsule endoscope in the retention space area.

4. The capsule endoscope storage case according to claim 3, wherein one of the first retainer and the second retainer is accommodated in the other one of the first retainer and the second retainer.

5. A capsule endoscope storage case for accommodating a capsule endoscope whose power supply can be operated by a predetermined magnetic force disposed within an operable range of a switch of the power supply, the capsule endoscope storage case comprising:

a blister pack having an outside storage portion for accommodating the capsule endoscope therein;
an inner cover portion included in the blister pack and having an inside storage portion in which the capsule endoscope is retained with the blister pack;
a sterilizing sheet having a sterilizing gas permeability and provided on a face of the blister pack to close an opening of the blister pack; and
a shield fixed to a first portion of the blister pack to prevent the predetermined magnetic force from affecting the switch through the first portion, wherein
a dimension of the outside storage portion in portions of the blister pack other than the first portion is larger than a dimension of the operable range of the switch of the power supply.

6. The capsule endoscope storage case according to claim 5, wherein a passage and a retention space area communicated with the passage are formed between the blister pack and the inner cover portion for accommodating and retaining the capsule in the retention space area so that a sterilizing gas may invade into the retention area through the passage to perform gas sterilization.

* * * * *